US 8,649,851 B2

(12) United States Patent
Cholette

(10) Patent No.: US 8,649,851 B2
(45) Date of Patent: Feb. 11, 2014

(54) METHOD AND SYSTEM FOR QUANTITATIVE MEASURE OF CURRENT OF INJURY DURING LEAD FIXATION

(75) Inventor: Martin Cholette, Acton, CA (US)

(73) Assignee: Pacesetter, Inc., Sylmar, CA (US)

( * ) Notice: Subject to any disclaimer, the term of this patent is extended or adjusted under 35 U.S.C. 154(b) by 343 days.

(21) Appl. No.: 12/882,597

(22) Filed: Sep. 15, 2010

(65) Prior Publication Data

US 2012/0065529 A1    Mar. 15, 2012

(51) Int. Cl.
*A61B 5/04* (2006.01)
(52) U.S. Cl.
USPC .......................................................... 600/509
(58) Field of Classification Search
USPC .......................................................... 600/510
See application file for complete search history.

(56) References Cited

U.S. PATENT DOCUMENTS

| 6,714,806 B2 | 3/2004 | Iaizzo et al. |
| 2003/0199938 A1 | 10/2003 | Smits et al. |
| 2004/0267326 A1* | 12/2004 | Ocel et al. .......................... 607/9 |

FOREIGN PATENT DOCUMENTS

| EP | 01322377 B1 | 3/2002 |
| WO | 0224063 A2 | 3/2002 |
| WO | 0224063 A3 | 6/2002 |

OTHER PUBLICATIONS

Saxonhouse et al.; "Current of Injury Predicts Adequate Active Lead Fixation in Permanent Pacemaker/Defibrillation Leads"; Journal of the American College of Cardiology, vol. 45, No. 3, 2005.*

* cited by examiner

*Primary Examiner* — Carl H Layno
*Assistant Examiner* — Paula J Stice

(57) ABSTRACT

The invention is directed towards measuring current of injury (COI) during lead fixation. A baseline waveform is sensed from a lead while the lead is in a pre-fixation position. The baseline waveform represents an interface between the lead and tissue proximate a lead prior to active fixation. Cardiac signals are then sensed when the lead is in a post-fixation position. The post-fixation waveform represents an interface between the lead and the tissue once the lead is actively attached to the tissue. A COI is calculated based on an automatic comparison of the baseline and post-fixation waveforms. A COI feature of interest is identified in the baseline and post-fixation waveforms and a COI index, a COI area, a COI differential and/or a COI ratio is calculated based on the COI feature of interest in the baseline and post-fixation waveforms.

22 Claims, 13 Drawing Sheets

METHOD AND SYSTEM FOR QUANTITATIVE MEASURE OF CURRENT OF INJURY DURING LEAD FIXATION

FIELD OF THE INVENTION

Embodiments of the present invention generally relate to methods and systems for measuring current of injury (COI) during lead fixation.

BACKGROUND OF THE INVENTION

An implantable medical device is implanted in a patient to monitor, among other things, electrical activity of a heart and to deliver appropriate electrical therapy, as required. Implantable medical devices ("IMDs") include, for example, pacemakers, cardioverters, defibrillators, implantable cardioverter defibrillators ("ICD"), and the like. The electrical therapy produced by an IMD may include, for example, the application of stimulation pulses including pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm.

When an IMD is implanted, one or more leads are located within or proximate to the heart. In many applications, active fixation cardiac leads are implanted. The leads may represent bradycardia or tachycardia leads. During the implantation process, the physician seeks to consistently implant leads at a desired position and with a desired degree of fixation within the cardiac tissue in order to maintain long term stability. A high level of skill and experience is generally required by the physician in order to consistently implant leads for long term stability. During implantation, the physician may be unduly conservative and not sufficiently affix the fixation element of an implantable lead into the myocardial tissue. Insufficient attachment of the fixation element to the myocardial tissue may lead to early dislodgement of the lead. Conversely, the physician may be unduly aggressive and over extend a helix from the lead into the cardiac tissue. Excessive helix extension potentially could lead to certain undesirable consequences such as coring, excessive tissue damage, perforation, micro perforation and the like. Typically, leads provide a very low degree of tactile feedback while the physician is actively attaching a helix to the tissue. This low degree of tactile feedback increases the difficulty for the physician in deciding how much to extend the lead helix.

Heretofore, no objective measure has been available to the physician, during lead implantation that could inform the physician regarding the extent to which a lead fixation element is properly secured to the myocardial tissue. A need remains for a mechanism to provide fixation related information to the physician that will assist the physician to provide more consistent fixation and increase safety to patients during implantation and post IMD implantation.

In accordance with certain embodiments, methods and systems are provided for measuring current of injury (COI) during lead implantation. The methods and systems sense cardiac signals from a lead within a chamber of the heart while the lead is in a pre-fixation position and capture a baseline waveform from the cardiac signals while the lead is in the pre-fixation position. The baseline waveform represents an interface between the lead and a tissue region proximate a tip of the lead before the lead is actively attached to the tissue region of the heart. The methods and systems sense cardiac signals from the lead within the chamber of the heart when the lead is in a post-fixation position and capture a post-fixation waveform from the cardiac signals when the lead is in the post-fixation position. The post-fixation waveform represents an interface between the lead and the tissue region proximate the tip of the lead after the lead is actively attached to the tissue region of the heart. The methods and systems calculate a COI indicator based on an automatic comparison of the baseline and post-fixation waveforms.

SUMMARY

In accordance with one embodiment, a method is provided for measuring current of injury (COI) during lead fixation. The method comprises sensing cardiac signals from a lead within a chamber of the heart while the lead is in a pre-fixation position and capturing a baseline waveform from the cardiac signals while the lead is in the pre-fixation position. The baseline waveform is representative of an interface between the lead and a tissue region proximate a tip of the lead before the lead is actively attached to the tissue region of the heart. The method further comprises sensing cardiac signals from the lead within the chamber of the heart when the lead is in a post-fixation position and capturing a post-fixation waveform from the cardiac signals when the lead is in the post-fixation position. The post-fixation waveform is representative of an interface between the lead and the tissue region proximate the tip of the lead after the lead is actively attached to the tissue region of the heart. The method comprises calculating a COI indicator based on an automatic comparison of the baseline and post-fixation waveforms.

In accordance with one embodiment, a system is provided for measuring current of injury (COI) during lead fixation. The system comprises inputs for sensing cardiac signals from a lead within a chamber of the heart while the lead is in a pre-fixation position and memory for capturing a baseline waveform from the cardiac signals while the lead is in the pre-fixation position. The baseline waveform is representative of an interface between the lead and a tissue region proximate a tip of the lead before the lead is actively attached to the tissue region of the heart.

The system further comprises the inputs sensing cardiac signals from the lead within the chamber of the heart when the lead is in a post-fixation position and the memory for capturing a post-fixation waveform from the cardiac signals when the lead is in the post-fixation position. The post-fixation waveform is representative of an interface between the lead and the tissue region proximate the tip of the lead after the lead is actively attached to the tissue region of the heart. The system comprises a processor for calculating a COI indicator based on an automatic comparison of the baseline and post-fixation waveforms.

DETAILED DESCRIPTION

Figure 1:
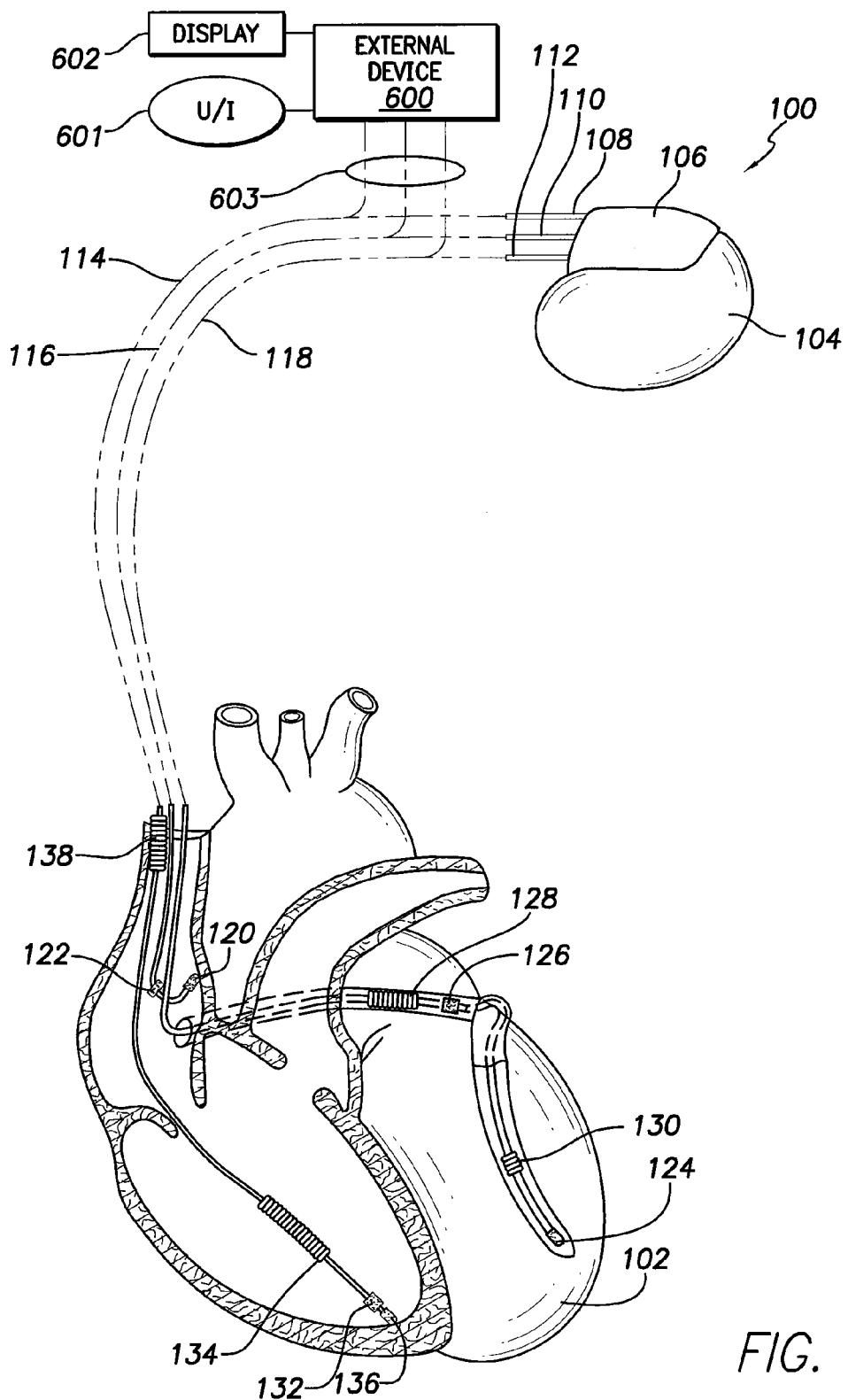
FIG. 1 illustrates an IMD and external device coupled to a heart in a patient and implemented in accordance with one embodiment.

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

When implanting an IMD, permanent pacing or defibrillation leads are positioned, such as through passive tines, by active fixation, or with a fixed or an extendable-retractable helix (collectively fixation elements). Often, the myocardial tissue undergoes a certain amount of localized injury while the fixation element is inserted. The localized injury is generally referred to as the current of injury. In general, the current of injury represents the flow of current to or from an injured tissue region of the heart due to regional alteration of the transmembrane potential at the point of fixation. Current of injury recognized at the site of tissue injury as an increase in the duration of the intracardiac electrogram (EGM) and/or in the elevation of the ST segment following a QRS complex. Current of injury has also been recorded during placement of passive leads. Passive leads may create trauma from electrode pressure against the endocardium which may damage cell membranes.

In at least one embodiment, an external device (e.g., a programmer) is connected to the lead during implantation. The programmer acquires bipolar IEGM signals and waits for a physician to press a "Capture" button on the user interface. When the Capture button is pressed, the external device captures the current IEGM waveform. When in the pre-fixation stage, the current IEGM waveform represents a baseline waveform. When in the post-fixation stage, the current IEGM waveform represents a post-fixation waveform.

The external device computes COI indicators (e.g., COI index, COI area, COI differential, and COI ratio) based on one or more pre-fixation or baseline waveforms and one or more post-fixation waveforms. The physician may press the Capture button multiple times throughout a lead fixation procedure in order to repeatedly obtain new waveforms that are representative of multiple steps of the fixation element in the fixation process. As a further option, the external device may automatically and continuously obtain new waveforms once the fixation process starts, thereby providing continuous real-time feedback representative of the current state of the fixation element on the lead.

During the fixation process, the external device may co-display captured waveforms (baseline and post-fixation). Before display, the external device aligns and scales the waveforms. For example, the waveforms may be aligned based on the peak of each R-wave. The waveforms may be displayed in a "sweep trigger manner", whereby the display is reset based on each R-wave. The external device may also display the COI index, COI area, COI differential, COI ratio and other COI indicators for the baseline and post-fixation waveforms.

Optionally, the external device may compute estimates for the lead fixation status. For example, the external device may determine whether the tine or helix on the lead is not yet affixed to tissue, partially affixed to tissue, fully affixed to tissue and the like. The external device may then display information indicative of the lead fixation status.

The external device may continue to capture waveforms and compute COI indicators until the physician presses an "End Fixation" button.

FIG. 1 illustrates an IMD 100 and external device 600 coupled to a heart 102 in a patient and implemented in accordance with one embodiment. The external device 600 may be a programmer, an external defibrillator, a workstation, a portable computer, a personal digital assistant, a cell phone and the like. The IMD 100 may be a cardiac pacemaker, an ICD, a defibrillator, an ICD coupled with a pacemaker, and the like, implemented in accordance with one embodiment of the present invention. The IMD 100 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structure for the IMD 100 is discussed and illustrated below in connection with FIG. 9.

The IMD 100 includes a housing 104 that is joined to a header assembly 106 that holds receptacle connectors 108, 110, 112 connected to a right ventricular lead 114, a right atrial lead 116, and a coronary sinus lead 118, respectively. The leads 114, 116, and 118 measure cardiac signals of the heart 102. The right atrial lead 116 includes an atrial tip electrode 120 and an atrial ring electrode 122. The coronary sinus lead 118 includes a left ventricular tip electrode 124, a left atrial ring electrode 126, and a left atrial coil electrode 128. The coronary sinus lead 118 also is connected with an LV ring electrode 130 disposed between the LV tip electrode 124 and the left atrial ring electrode 126. The right ventricular lead 114 has an RV tip electrode 136, an RV ring electrode 132, an RV coil electrode 134, and an SVC coil electrode 138. The leads 114, 116, and 118 detect IEGM signals that form an electrical activity indicator of myocardial function over multiple cardiac cycles.

During implantation, the external device 600 is connected to one or more of the leads 114, 116, 118 through temporary inputs 603. The inputs 603 of the external device 600 receive IEGM signals from the leads 114, 116, 118 during implantation and display the IEGM signals to the physician on display 602. Optionally, the external device 600 may not be directly connected to the leads 114, 116 and 118. Instead, the IEGM cardiac signals sensed by the leads 114, 116 and 118 may be collected by the IMD 100 and then transmitted wirelessly to the external device 600. Hence, the external device 600 receives the IEGM cardiac signals through telemetry circuit inputs. The physician or another user controls operation of the external device 600 through a user interface 601. Among other things, the external device 600 implements a current of injury measurement and assessment process during the lead implantation procedure as explained hereafter in connection with FIGS. 2-5. Exemplary structure for the external device 600 is discussed and illustrated below in connection with FIG. 6.

Figure 2A:
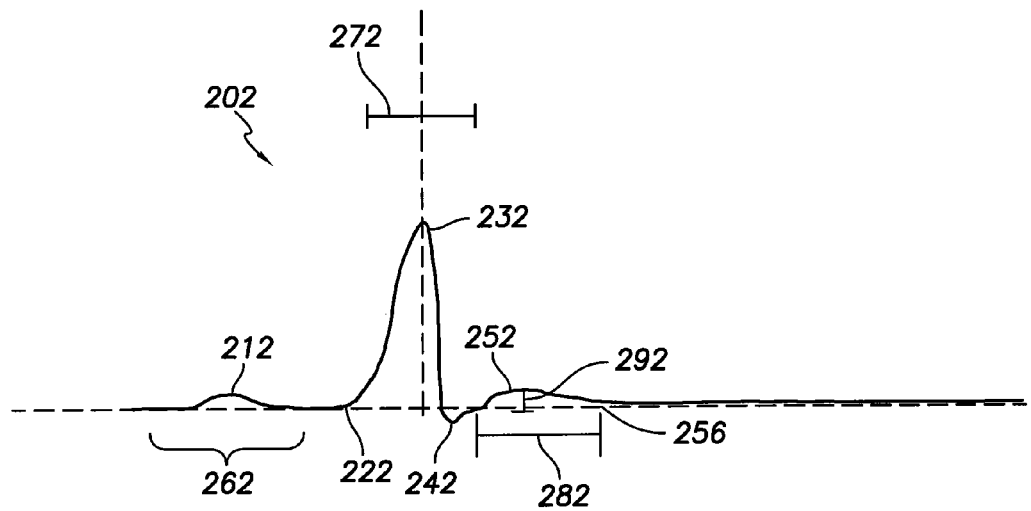
FIGS. 2A-2E illustrate examples of waveforms obtained at different times during implantation of one or more leads.
Figure 2B:
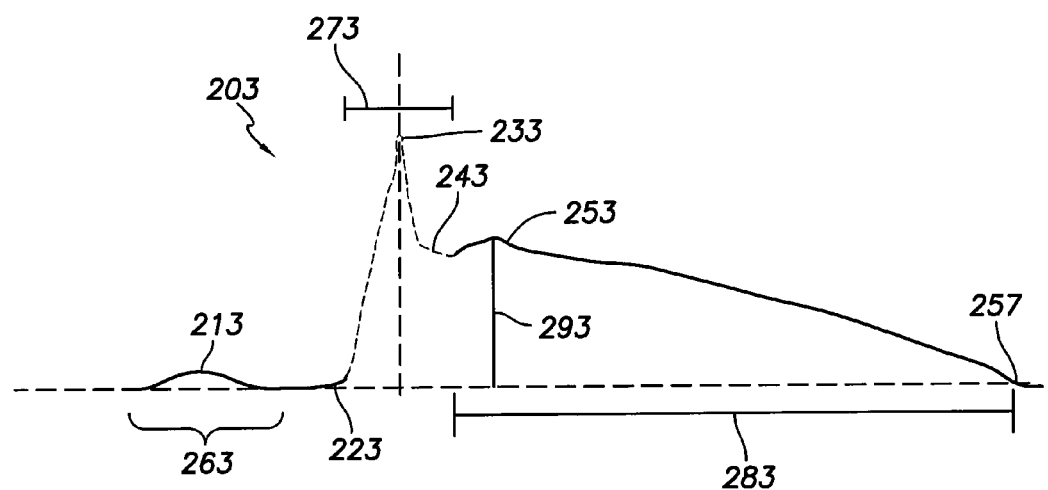
Figure 2C:
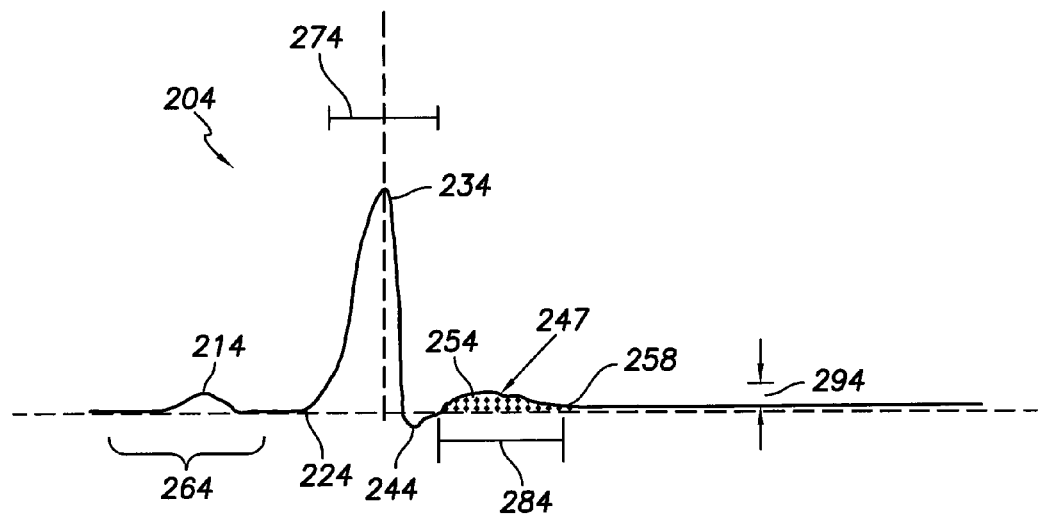
Figure 2D:
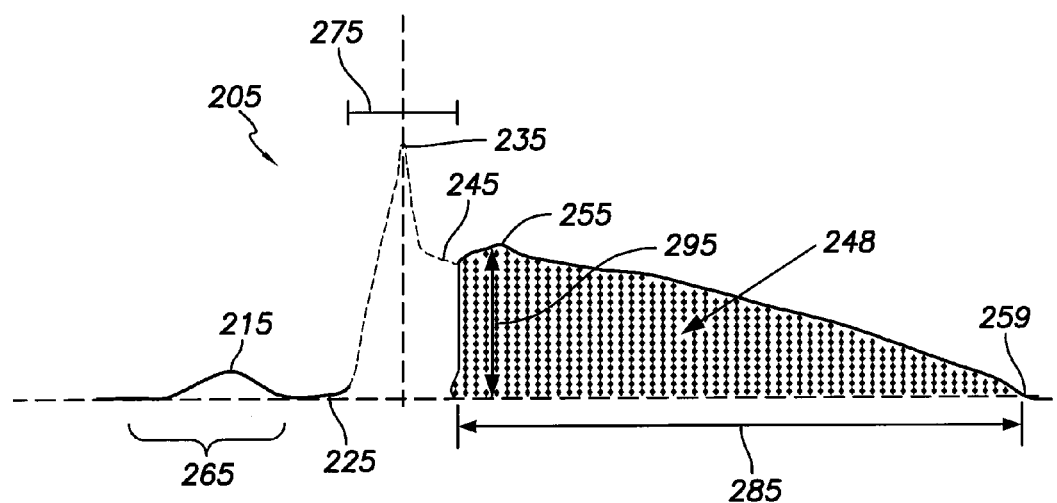
Figure 2E:
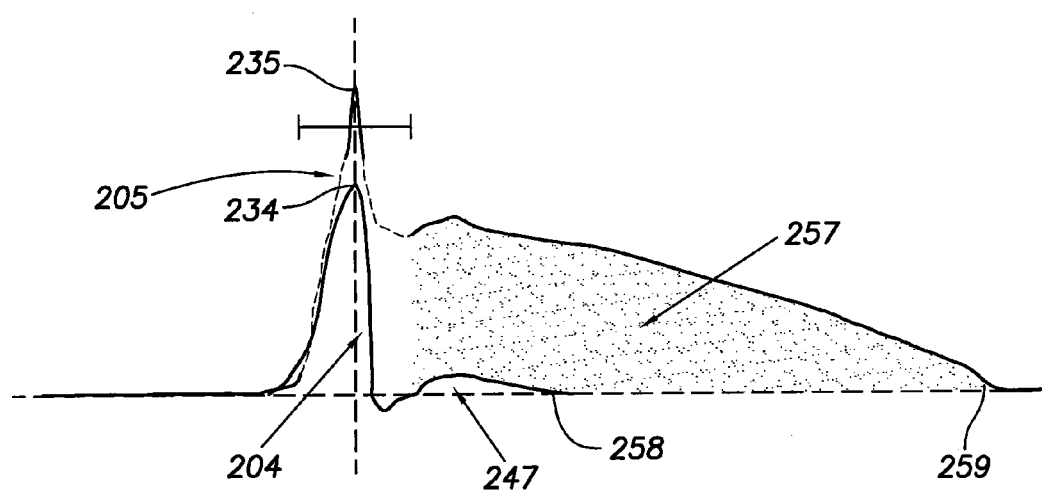

FIGS. 2A-2E illustrates examples of waveforms obtained at different times during implantation of one or more leads. FIGS. 2A and 2C represent pre-fixation or baseline waveforms 202 and 204 collected prior to securing a lead to cardiac tissue, while FIGS. 2B and 2D represent post-fixation 203 and 205 collected during or after the lead is partially or wholly affixed to the cardiac tissue. FIG. 2E illustrates the baseline and post-fixation waveform 204 and 205 overlaid upon one another after being scaled and aligned with one another. FIGS. 2A-2E includes a horizontal time axis and a vertical axis that defines units in voltage. The waveforms 202-205 include P-waves 212-215, Q-waves 222-225, R-waves 232-235, S-waves 242-245, and T-waves 252-255. The P-waves 212-215 represent atrial depolarization and may be used to characterize atrial activity of the heart 102. The R-waves 232-235 represent ventricular depolarization and may be used to characterize ventricular activity of the heart 102. The T-waves 252-255 represent the relaxation or repolarization of the heart 102.

As explained below, portions of the waveforms 202-205 are analyzed for various features of interest to derive different COI indicators. Each waveform 202-205 is segmented by the COI measurement process into isoelectric zones 262-265, exclusions zones 272-275 and ST-segment zones 282-285. The isoelectic zones 262-265 precede the exclusion zones 272-275 in time and the ST-segment zones 282-285 follow the exclusion zones 272-275 in time. The portions of the waveforms 202-205 within each zone 262-265, 272-275 and 282-285 are analyzed for different features of interest.

The exclusion zones 272-275 are established about the QRS complex of each waveform 202-205. Each exclusion zone 272-275 extends, by predetermined and/or programmed time periods, upstream (before) and downstream (after) from the peak of the corresponding R-waves 232-235. The peak of the R-wave 232-235 is used to scale the waveforms 202-205 to a common scale. The portions of the waveforms 202-205 within the exclusion zones 272-275 are not utilized when calculating current of injury (COI) indicators.

The isolectric zones 262-265 are established before (upstream) the exclusion zones 272-275 in time. Isoelectric zones 262-265 represent regions where the P-waves 212-242 are located. Each isoelectric zone 262-265 may be defined to have a predetermined or programmed length. Each isoelectric zone 262-265 may be positioned along the corresponding waveform 202-205 by centering (or otherwise positioning) the isoelectric zone 262-265 at the peak of the P-wave 212-215. Alternatively, the isoelectric zone 262-265 may be positioned by setting the beginning of the isoelectric zone 262-265 a predetermined or programmed time period before the peak of the corresponding R-wave 232-235 or a predetermined or programmed time period before the beginning of the corresponding exclusion zone 272-275. As explained below, the portions of the waveforms 202-205 in the isoelectric zones 262-265 are analyzed to establish the isoelectric level. The isoelectric level in each waveform 202-205 is used to align waveforms 202-205 with one another.

The ST-segment zones 282-285 include ST-segment durations that begin immediately after the exclusion zones 272-275 and continue until the corresponding waveform 202-205 crosses the zero voltage level which is denoted as the neutral crossing point 256-259. The ST-segment zones 282-285 include corresponding maximum ST-segment shifts 292-295 that extend from the horizontal axis (which represents the zero voltage level) up to the peak of the T-wave 252-255. As shown in FIGS. 2C and 2D, the ST-segment zones 284-285 include areas 247-248 under the corresponding portion of the waveform 204-205 that are indicative of the current of injury.

FIGS. 3 and 4A-4C illustrate a process carried out in accordance with an embodiment by the external device 600 or IMD 100 to measure current of injury during implantation and fixation of a lead. The process of FIGS. 3 and 4A-4C may be performed for only one, or repeated for each, of the leads 114, 116 and 118. For example, the process of FIGS. 3 and 4A-4C may be performed in connection with the lead 114, while the tip electrode 136 is actively affixed to the apex of the right ventricle. The process of FIGS. 3 and 4A-4C may be repeated when implanting the lead 118 in a coronary artery proximate to the left ventricle. The process of FIGS. 3 and 4A-4C may be repeated when implanting the lead 116 in the right atrium.

Figure 3:
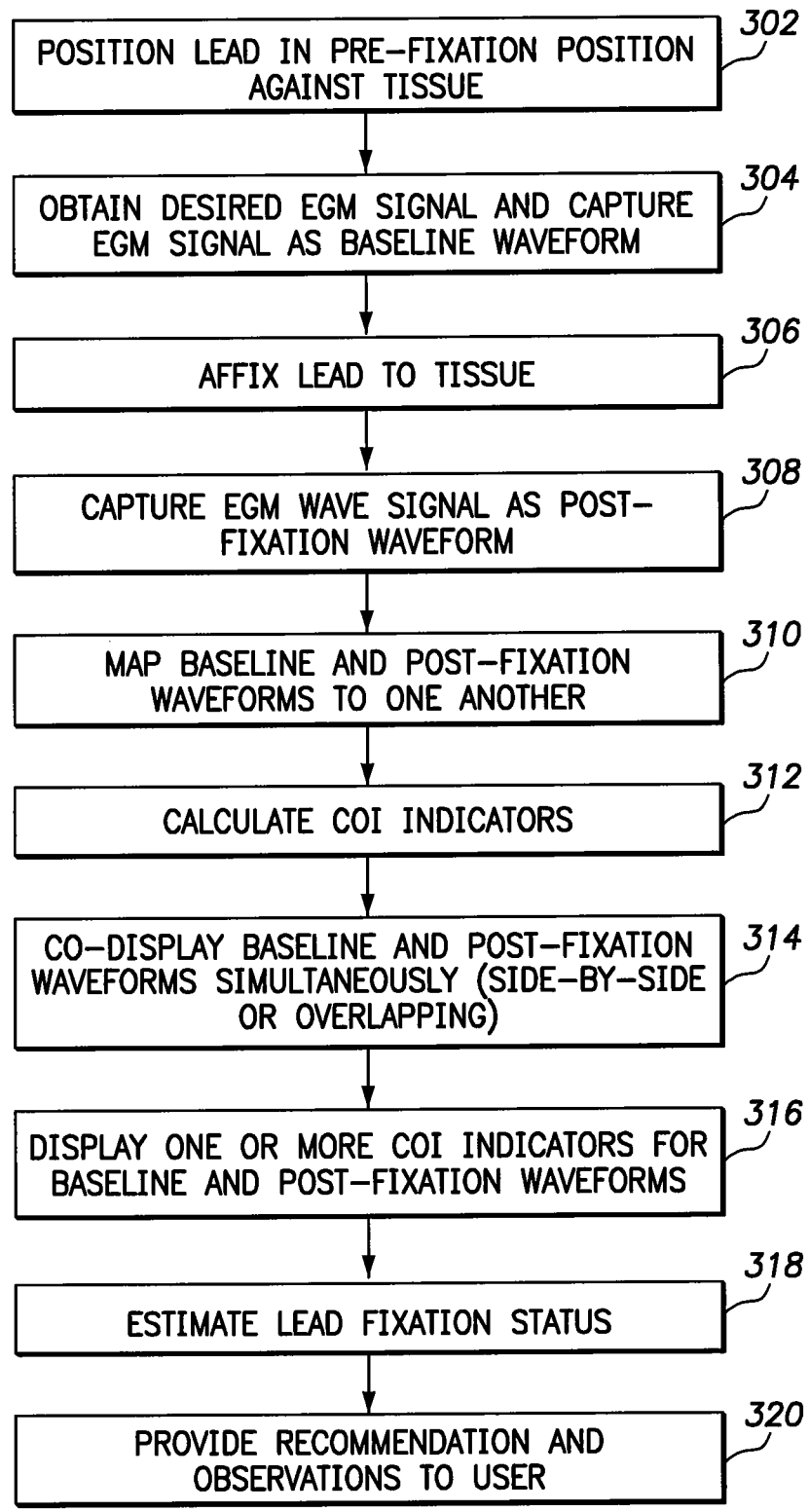
FIG. 3 illustrates a process to measure COI.

In FIG. 3, beginning at 302, a physician locates the lead (e.g. one of leads 114, 116 or 118) at a pre-fixation position within a chamber of the heart or within a coronary artery proximate to a chamber of the heart. For purposes of illustration only, the following example will be discussed in connection with implantation and fixation of the lead 118. It will be recognized that embodiments may be implemented with other types of leads and proximate to other regions/chambers of the heart. When in the pre-fixation position, a fixation element on the tip of the lead 118 is positioned immediately proximate to, or directly engaging, the desired tissue of the heart 102. The lead 118 is electrically coupled to an external device 600 that is configured to perform the operations described herein and to display the information described herein in accordance with various embodiments.

At 304, once the lead 118 is in the pre-fixation position, IEGM cardiac signals are collected and displayed on the external device 600 to the physician. The external device 600 is able to collect cardiac signals utilizing one or more electrode(s) on the lead 118. Optionally, the cardiac signals may be collected utilizing one or more electrodes on another lead (e.g., leads 114 and 116). The cardiac signals are sensed along one or more sensing vectors that are defined by one or more sensing electrodes. For example, the cardiac signals may be collected along a sensing vector defined between RV electrode 136 and RV electrode 134. Optionally, the cardiac signals may be collected along a sensing vector defined between RV electrode 136 and RA electrode 122. Optionally, the cardiac signals may be collected along a sensing vector defined between RV electrodes 134 and 136 (which may be electrically common) and an LA electrode 126 or an LV electrode 130. The sensed cardiac signals may resemble the pre-fixation waveform 202 in FIG. 2A.

The inputs of the external device 600 may collect a single waveform 202 once the lead 118 is in a desired pre-fixation position. Optionally, the external device 600 may collect continuously collect waveforms 202 while the physician adjusts the position of the lead 118. As the position of the lead 118 is adjusted, the waveforms 202 will change shape. The physician may repeatedly adjust the position of the lead 118 until a desired waveform 202 is collected and displayed.

When a desired IEGM cardiac signal is displayed, such as the waveform 202 in FIG. 2A, the physician selects the waveform 202 through an entry on the user interface 601. For example, the physician may press a "Capture" button on the user interface 601 of the external device 600, thereby directing the external device 600 to capture the IEGM cardiac signal as a baseline waveform. The baseline waveform 202 represents a pre-fixation waveform which corresponds to cardiac signals collected prior to actively attaching the fixation element on the tip of the lead 118 to the tissue region of the heart. The baseline waveform 202 is saved in memory of the external device.

At 306, the physician secures or affixes the fixation element on the tip of the lead 118 to the tissue region. Fixation may be achieved by anchoring the lead 118 to the heart tissue either by passively using tines or by active fixation. For example, active fixation may include a fixed, or an extendable retractable helix, that is rotated to be secured to the myocardial tissue. The act of fixating the lead 118 to the myocardial tissue causes a local, minor alteration of the transmembrane potential. The alteration of the transmembrane potential affects the flow of current to and from the altered region.

At 308, once the lead 118 is affixed to the tissue, cardiac signals are collected. During post-fixation, the external device 600 may collect a single cardiac signal or may continuously collect EGM cardiac signals. The IEGM cardiac signals are displayed to the physician during the fixation process and after the physician ceases adjusting/rotating the fixation element. During the fixation process or after, the physician reaches a desired stage of fixation with the lead 118, a user enters a waveform capture command at the user interface 601 of the external device 600. For example, the user may press a "Capture" button on the user interface 601, thereby capturing an IEGM cardiac signal as the post-fixation waveform. The post-fixation waveform reflects a state or condition of the tissue region proximate to the tip of the lead 118 after the lead 118 has been wholly or partially secured or actively attached to the heart tissue. The sensed cardiac signals may resemble the post-fixation waveform 203 in FIG. 2B.

At 310, the process maps the baseline and post-fixation waveforms 202 and 203 onto one another based on features of interest from each of the baseline and post-fixation waveforms 202 and 203.

Figure 4A:
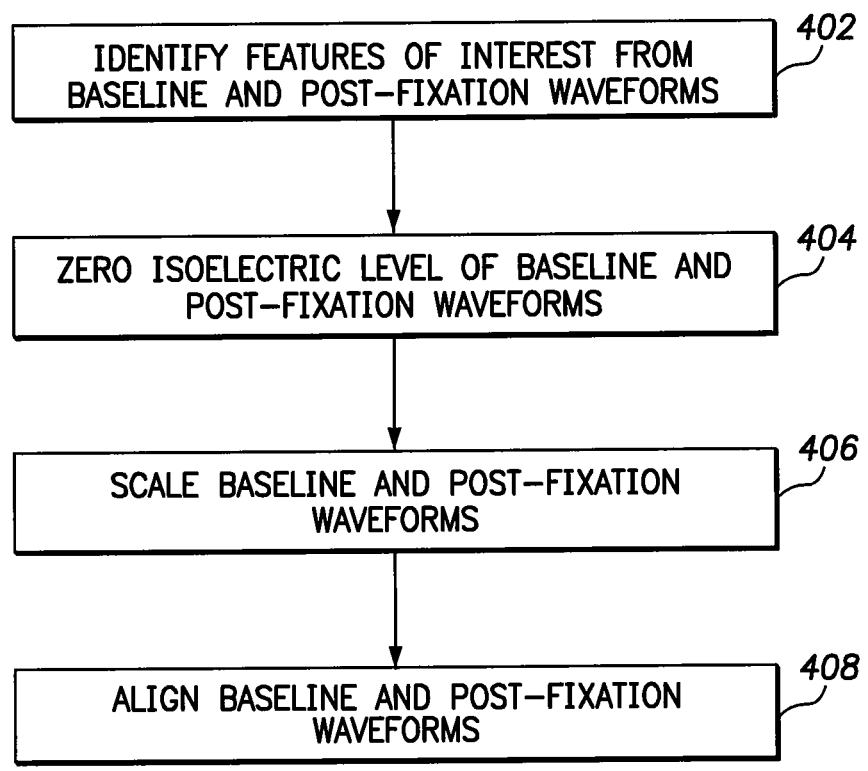
FIG. 4A illustrates a process for mapping post-fixation waveforms onto a baseline waveform in accordance with an embodiment.

FIG. 4A illustrates a process for mapping post-fixation waveforms 203 onto a baseline waveform 202 in accordance with an embodiment. At 402, one or more features of interest are identified from each of the baseline waveform 202 and the post-fixation waveform 203. For example, the features of interest may include the peaks of the P-waves 212-213, R-waves 232-233, T-waves 252-253, zero crossing points for one or more of the P-waves 212-213, R-waves 232-233, T-waves 252-253 and the like.

At 404, isoelectric levels for the baseline waveform 202 and the post-fixation waveform 203 are identified and "zeroed" along the vertical axis by adjustment to match the horizontal axis. The isoelectric level for a particular waveform is measured from the waveform. By way of example, the isoelectric leveling FIGS. 2A-2B may correspond to a minimum or average level of the PQ segment within the isoelectric zone 262-263. Optionally, the isoelectric level may correspond to a level in the baseline or post-fixation waveform 202 or 203 measured at a predetermined time following the peak of the P-wave 212-213. As a further example, the isoelectric level may correspond to a level in the baseline or post-fixation waveform 202 or 203 that is measured a predetermined time before the peak of the P-wave 212-213. In one embodiment, a separate isoelectric level is identified for each baseline waveform and a separate isoelectric level is identified for each post-fixation waveform. Alternatively, a cumulative isoelectric level may be formed based on a group of baseline waveforms.

Figure 4B:
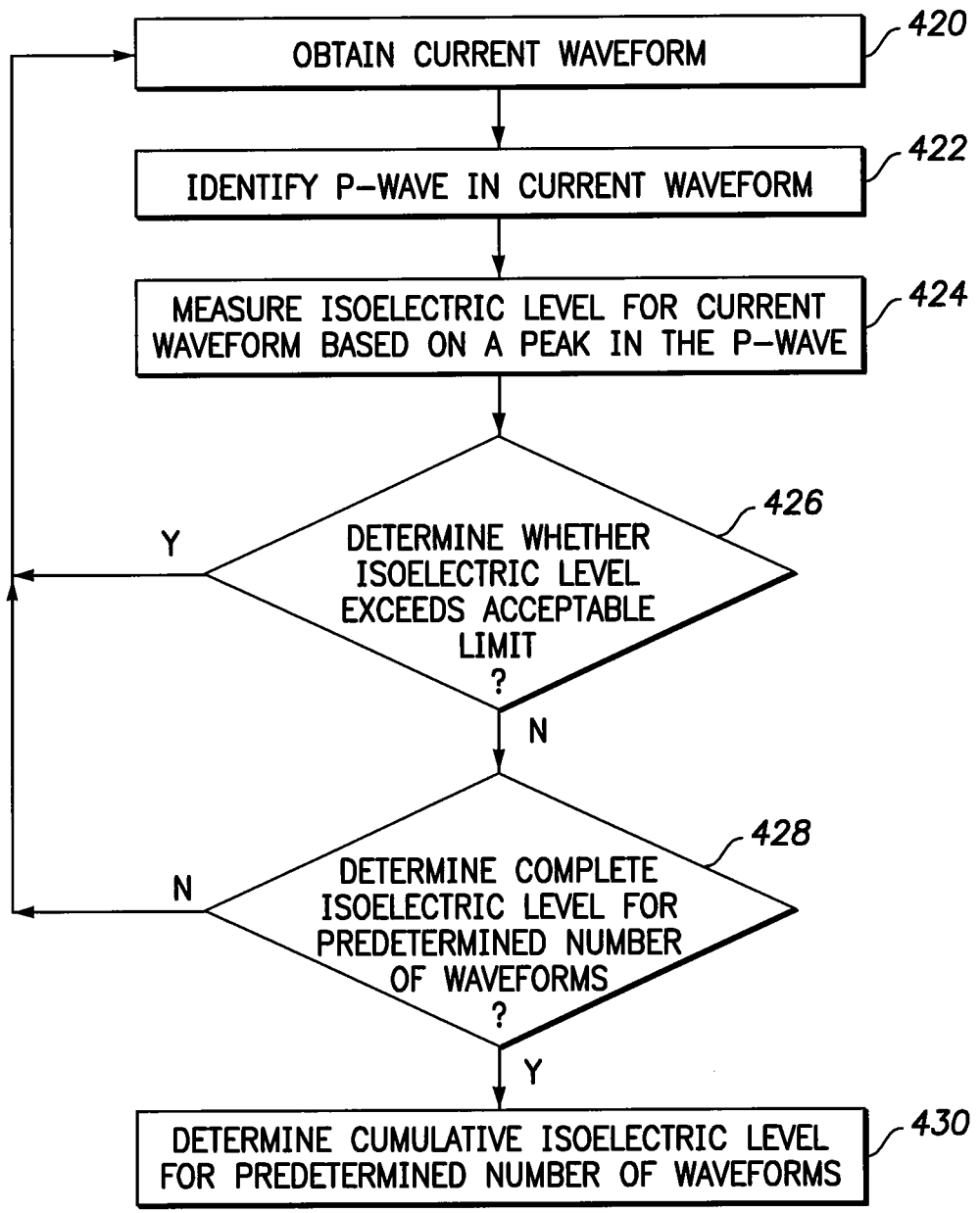
FIG. 4B illustrates a processing sequence carried out in accordance with an alternative embodiment for identifying isoelectric levels based on one or more waveforms.

FIG. 4B illustrates a processing sequence carried out in accordance with an alternative embodiment for identifying isoelectric levels based on one or more waveforms. Beginning at 420, a waveform of interest is obtained (e.g. a first baseline waveform). At 422, the P-wave within the waveform is identified. At 424, the isoelectric level is measured from the waveform. By way of example, the isoelectric level may correspond to a level of the waveform measured at a predetermined time following the peak of the P-wave. As a further example, the isoelectric level may correspond to a level in the waveform that is measured a predetermined time before the peak of the P-wave. Optionally, the isoelectric level may correspond to an average level of the PQ segment.

At 426, the measured isoelectric level is analyzed to determine whether the isoelectric level (determined at 422) is too high to represent an actual isoelectric level. When the measured isoelectric level is determined to be outside of acceptable limits at 426, the waveform is erased and operation returns to 420 where a new waveform is collected. When the isoelectric level is determined at 426 to fall within acceptable tolerances, flow moves to 428.

At 428, it is determined whether it is desirable to collect additional waveforms in connection with determining the isoelectric level. For example, when determining the baseline isoelectric level, it may be desirable to collect a series of waveforms over multiple cardiac cycles before fixation of a lead (e.g., 10 seconds, 10 cardiac cycles, and the like). The operations at 420-426 are repeated until it is determined, at 428, that the predetermined number of waveforms has been collected.

Next, flow moves to 430 where the isoelectric levels of the previously collected waveforms are combined to form a cumulative isoelectric level. For example, the cumulative baseline isoelectric level may represent an average isoelectric level for the 5-10 baseline waveforms collected prior to lead fixation. Alternatively, the cumulative baseline isoelectric level may correspond to a mean, a median, a mode or some other statistical representation derived from the isoelectric level measurements for the predetermined number of waveforms.

The operations of FIG. 4B may be repeated to determine the isoelectric level of a post-fixation waveform. However, each post-fixation waveform may have a separate isoelectric level. Hence, when capturing a post-fixation waveform, the isoelectric level will generally be derived from and associated with a single post-fixation waveform. Thus, flow will pass from 428 to 430 after a single post-fixation waveform is captured. Once baseline and post-fixation isoelectric levels are determined, flow returns to the mapping process of FIG. 4A.

Returning to FIG. 4A, at 406, the baseline and post-fixation waveforms 202 and 203 are aligned with one another based on a feature of interest. For example, the alignment feature of interest may represent the peak of the R-waves 232-233. The baseline and post-fixation waveforms 202 and 203 are then overlapped on a common horizontal axis (time axis) and shifted along the horizontal axis until the R-waves 232-233 coincide temporally at a common point in time. Optionally, the baseline and post-fixation waveforms 202 and 203 may be temporally aligned based on another feature of interest, such as the peak of the P-wave 212-213, peak of the T-wave 252-253, the duration of the QRS complex, the ST-segment and the like.

At 408, the baseline and post-fixation waveforms 202-203 are scaled to a common scale. For example, a scaling feature or interest may be identified from each of the baseline and post-fixation waveforms 202-203. By way of example, the scaling features may be the peaks of the P-waves 212-213, the Q-waves 222-223, the R-waves 232-233 the S-waves 242-243 the T-waves 252-253 and the like. Optionally, the scaling features may be the average level for the PQ segment or the average level of the ST segment. Optionally, the scaling features may be the difference between the isoelectric level (determined in 404) and the peak of the P-wave 212-213, or the difference between the isoelectric level and the peak of the R-wave peak 232-233.

Optionally, the operations of FIGS. 4A and 4B may be performed with respect to the baseline waveform 202 separate in time from the operations of FIGS. 4A and 4B with respect to the post-fixation waveform 203. For example, the isoelectric level, alignment feature and scaling feature of the baseline waveform 202 maybe determined at or after the operations of 304 in FIG. 3 before fixation of the lead 118 and before collecting the post-fixation waveform 203. Once the baseline and post-fixation waveforms 202-203 are mapped onto one another based on isoelectric levels, alignment and scale, flow returns to 312 in FIG. 3.

Returning to FIG. 3, at 312, the baseline and post-fixation waveforms are automatically compared with one another in order to calculate one or more COI indicators. Various COI indicators may be calculated, such as the COI index, COI area, COI differential, COI ratio and the like. Exemplary processes for calculating the COI indicators are illustrated and described below in connection with FIGS. 2A-2E and 4C.

At 314, the baseline and post-fixation waveforms 202-203 are co-displayed. For example, the baseline and post-fixation waveforms 202-203 may be presented immediately adjacent to one another (side by side) on a common monitor. Optionally, the baseline and post-fixation waveforms 202-203 may be presented on separate but adjacent monitors. Alternatively, the baseline and post-fixation waveforms 202-203 may be displayed simultaneously, in an overlaid manner, on common horizontal and vertical axes with the peaks of the R-waves 232-233 temporally aligned with one another (as in FIG. 2E).

At 316, additional COI indicators may be displayed, such as the COI index, COI area, COI differential and/or COI ratio. The COI indicators presented at 316 are derived from the baseline waveform and one or more post-fixation waveforms.

At 318, the process may automatically analyze a status of the lead fixation. For example, at 318, one or more of the COI indicators may be compared with COI thresholds for the corresponding COI indicators. When the value of a COI indicator exceeds a corresponding COI threshold, it may be determined at 318 that the lead is adequately affixed to the heart tissue.

At 320, the process may provide observations and/or recommendations to the physician. For example, at 320, the process may inform the physician of the present values for one or more COI indicators. Optionally, in addition or alternatively, the process may suggest to the physician to further advance the fixation element by a variable or set distance or variable set rotation amount. Optionally, the recommendation may suggest to the physician to stop rotating the fixation element. Optionally, the recommendation may inform the physician of a suggested number of additional turns of a helix. It should be realized that in many embodiments, the operations at 318 and 320 may be entirely removed and not performed at all. Instead, the process may not perform any type of determination regarding fixation status, and may not provide any recommended action to the physician.

Figure 4C:
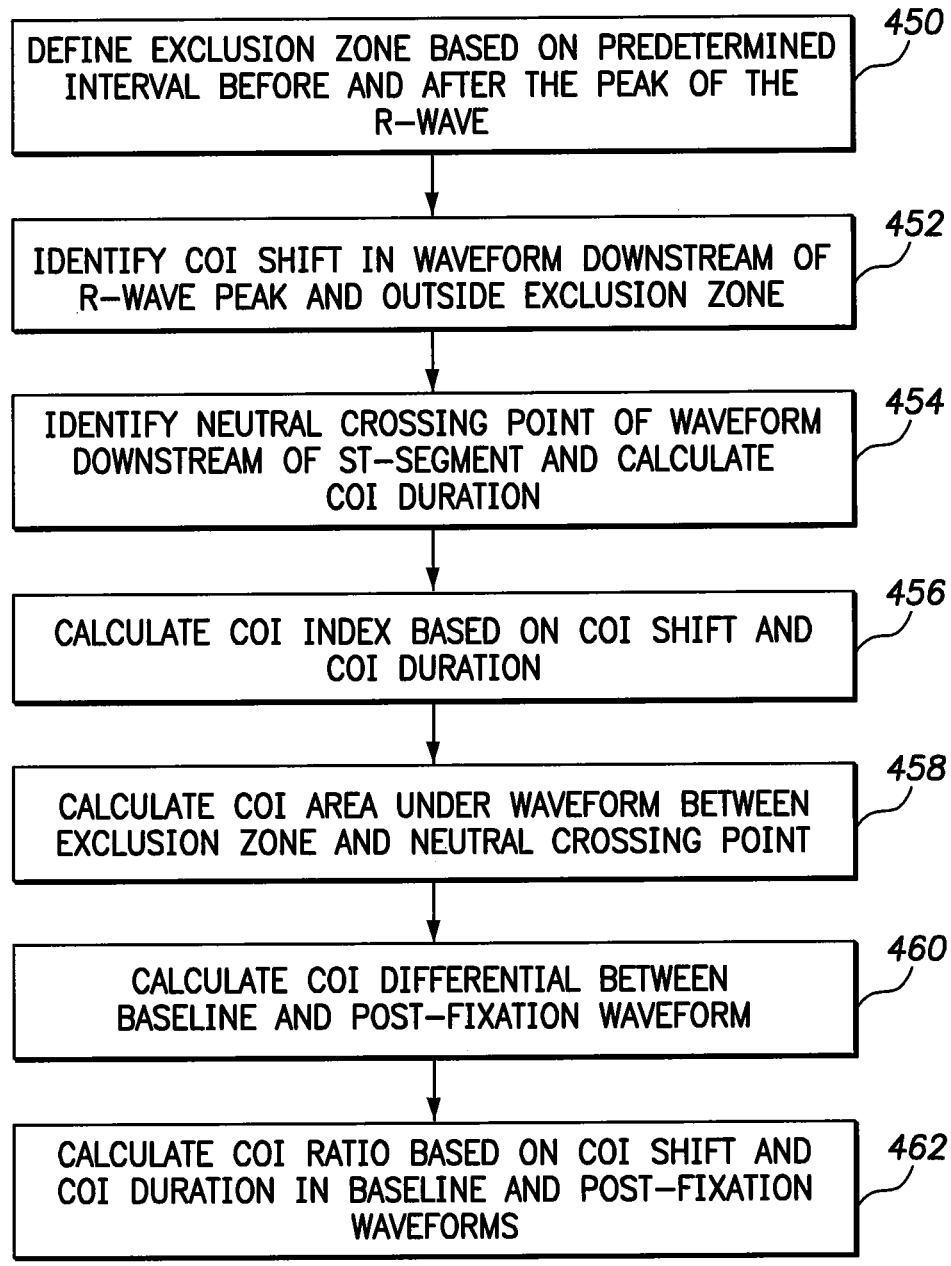
FIG. 4C illustrates a process for calculating exemplary COI indicators in accordance with an embodiment.

FIG. 4C illustrates a process carried out in accordance with an embodiment for calculating exemplary COI indicators. Beginning at 450, an exclusion zone is identified within the baseline and post-fixation waveforms. The exclusion zone may extend a predetermined interval before and after the peak of the R-wave. By way of example, the predetermined interval may be programmed by a user, set at the time of manufacture or automatically derived by the external device during operation.

At 452, COI shifts are identified in the baseline and post-fixation waveforms. The COI shift in an individual waveform occurs downstream of the R-wave peak after or outside of the exclusion zone. By way of example, the COI shift may represent an ST segment shift that is measured in the baseline and post-fixation waveforms. The COI shift extends from the isoelectric level to a peak in the waveform following the exclusion zone. In the examples of FIGS. 2A and 2B, the baseline and post-fixation waveforms 202 and 203, include COI shifts 292 and 293, respectively. The COI shifts 292 and 293 extend from the isoelectric level to the peak of the T-waves 252 and 253, respectively. As is evident in FIGS. 2A and 2B, the peak of the T-wave 253 is substantially greater than the peak of the T-wave 252.

Returning to FIG. 4C, at 454, neutral crossing points are identified in each of the baseline and post-fixation waveforms. The neutral crossing point of each waveform occurs downstream of the COI shift (e.g., downstream of the ST segment shift). It should be realized that the waveform may cross, at the neutral crossing point, from a positive to a negative level, or from a negative to a positive level, depending upon the polarity of the sensed signals. Once the neutral crossing point is identified from the waveform, a COI duration is calculated. In the examples of FIGS. 2A and 2B, the process of FIG. 4C would identify the neutral crossing points 256 and 257, and the COI durations 282 and 283, respectively. The COI duration 282 and 283 begins at the end of the exclusion zones 272 and 273 and extend to the neutral crossing points 256 and 257, respectively. As is evident in FIGS. 2A and 2B, the COI duration 282 in the baseline waveform 202 is much shorter than the COI duration 283 in the post-fixation waveform 203.

Returning to FIG. 4C, at 456, a COI index for the baseline waveform and a COI index for the post-fixation waveform are calculated based on the COI shifts and the COI durations. By way of example only, each COI index may represent the product of the COI shift and the COI duration of the corresponding waveform. The COI index for the baseline waveform and the COI index for the post-fixation waveform may be displayed to the physician on the external device 600 as an indication of the extend, to which the fixation element has altered the corresponding tissue region.

At 458, COI areas are calculated for the baseline and post-fixation waveforms. The COI area represents the area under the corresponding waveform beginning at the end of the exclusion zone and continuing up until the waveform neutral crossing point. FIGS. 2C and 2D illustrate exemplary baseline and post-fixation waveforms 204 and 205 for which the COI areas 247 and 257, respectively, are calculated. The COI area 247 in the baseline waveform 204 is substantially smaller than the COI area 257 for the post-fixation waveform 205. The baseline and post-fixation waveforms 204 and 205 and the COI areas 247 and 257 may be displayed to the physician on the external device 600 as another indicator of the extent, to which the fixation element has altered the tissue region.

At 460, a COI differential is calculated between the COI areas in the baseline and post-fixation waveforms. For example, the COI area of the baseline waveform may be subtracted from the COI area of the post-fixation waveform in order to determine the COI differential. FIG. 2E illustrates an example of how a COI differential may be displayed to the physician on the external device 600. In FIG. 2E, baseline and post-fixation waveforms 204 and 205 are mapped onto one another (e.g., isoelectric levels are matched, scaled, aligned). The R-waves 234 and 235 are aligned and scaled. The ST segments are overlaid and the COI difference between the COI areas 256 and 257 is highlighted.

At 462, a COI ratio is calculated based on the COI shift and COI duration in the baseline and post-fixation waveforms. By way of example only, the COI ratio may equal the (post-fixation COI shift)/(baseline COI shift)*(post-fixation COI duration)/(baseline COI duration). Optionally, other mathematical relations may be applied to compare the baseline and post-fixation COI shifts. Optionally, other mathematical relations may be applied to compare the baseline and post-fixation COI durations.

Optionally, the processes of FIGS. 3 and 4A-4C may be repeated for multiple post-fixation waveforms (e.g., repeated at user determined times, continuously, etc.). Optionally, different interim-fixation waveforms may be compared to one another through the processes of FIGS. 3 and 4A-4C. Interim-fixation waveforms may be processed as baseline waveforms or post-fixation waveforms. In this alternatively embodiment, an interim-fixation waveform obtained earlier in time (e.g. when the fixation element is only slightly affixed to the tissue) may be treated as a "baseline" waveform and an interim-fixation waveform obtained later in time (e.g. when the fixation element is more securely affixed to the tissue) may be treated as a "post-fixation" waveform. The terms baseline waveform and post-fixation waveform shall encompass interim-fixation waveforms.

Figure 5:
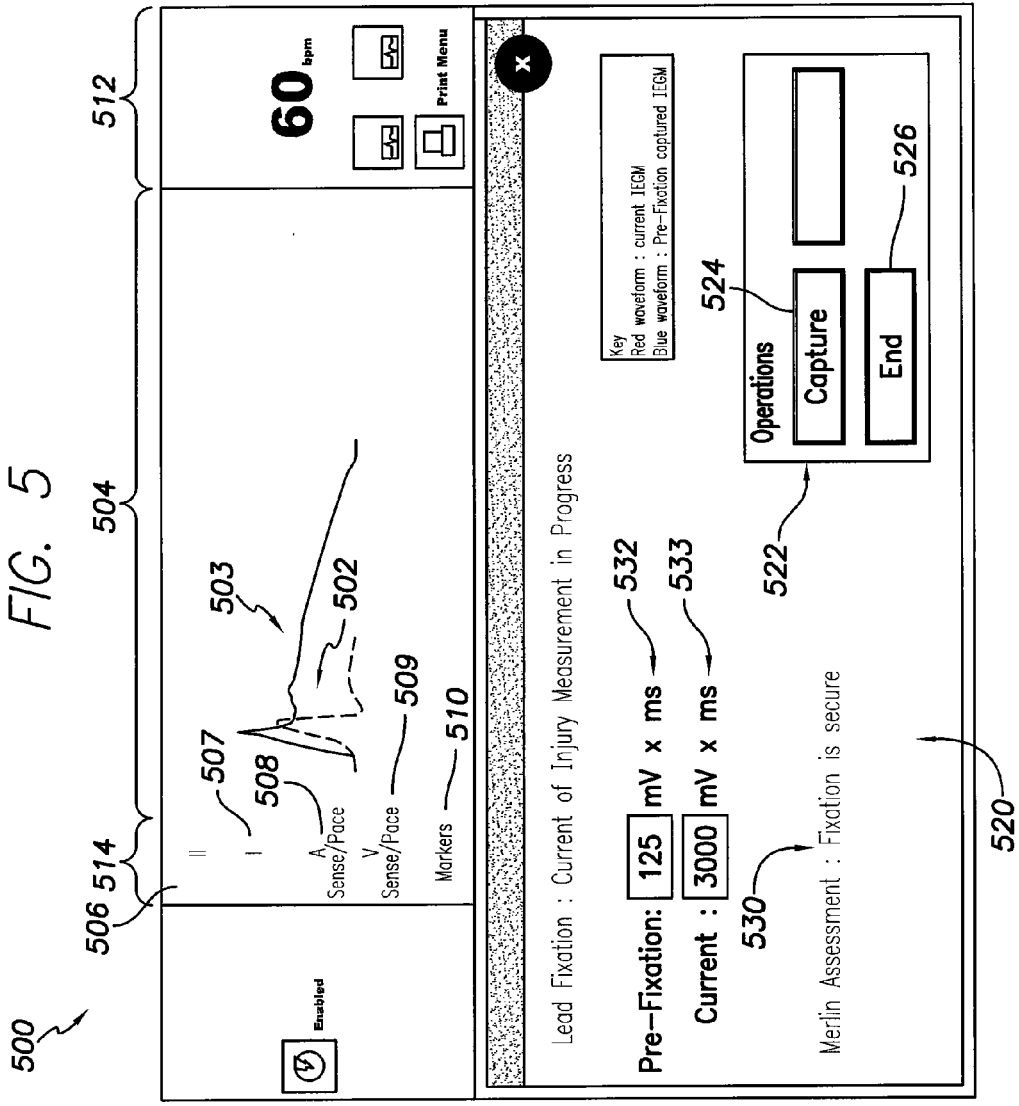
FIG. 5 illustrates an exemplary screen shot of a display that may be presented on the external device.

FIG. 5 illustrates an exemplary screen shot of a display that may be presented on the external device 600. The screen shot includes a window 500 having a waveform region 504, a waveform control region 514, patient general status region 512, a COI indicator region 520, and a COI control region 522. The waveform region 504 displays a baseline waveform 502 and a post-fixation waveform 503 overlaid on a common time axis. The waveform control region 514 includes soft keys (touch sensitive areas on the display) 506-510 that control the information displayed in the waveform region 504 (e.g. atrial sense/pace, ventricular sense/pace, display markers, electrode configuration I, electrode configuration II, and the like). The status region 512 displays general patient information such as the heart rate and the like.

The COI indicator region 520 includes a header indicating that a current of injury measurement is in progress. The COI indicator region 520 may illustrate various COI indicators. In the example of FIG. 5, the COI index 532 and the COI index 533 are illustrations for baseline and post-fixation, respectively. As explained above, the COI indices 532 and 533 represent the product of the COI shift and COI duration for corresponding waveforms.

Optionally, an assessment field 530 may be included to provide a recommendation or observation regarding lead fixation status. For example, COI thresholds may be stored in the external device 600, and compared with the COI indicators. Different assessment messages may be stored and associated with different situations based on when a particular COI indicator falls within certain limits or exceeds a COI threshold. For example, if the COI index is below a minimum threshold, the assessment message may be that the fixation element has not yet engaged the tissue. If the COI index then falls within an acceptable range, the assessment message may be that the fixation element is secure. If the COI index exceeds an upper threshold, then the assessment message may be a warning that the fixation element is potentially extended to far. Optionally, assessment messages may be associated with limits or thresholds for each of the COI area, COI differential, COI ratio and the like. The window 500 may simultaneously display multiple assessment messages associated with different COI indicators.

Optionally, the assessment message may be based on a combination of COI indicators. For example, the message that "fixation is secure" may only be displayed when 2 or more of the COI indicators meet corresponding COI thresholds.

The COI control region 522 includes inputs to control the COI measurement process of FIGS. 3 and 4A-4C. A CAPTURE button 524 may be pressed when the physician wants to capture a new waveform (e.g., a new baseline or post-fixation waveform). An END button 526 may be pressed by the physician when the COI measurement process of FIGS. 3 and 4A-4C is completed.

Figure 6:
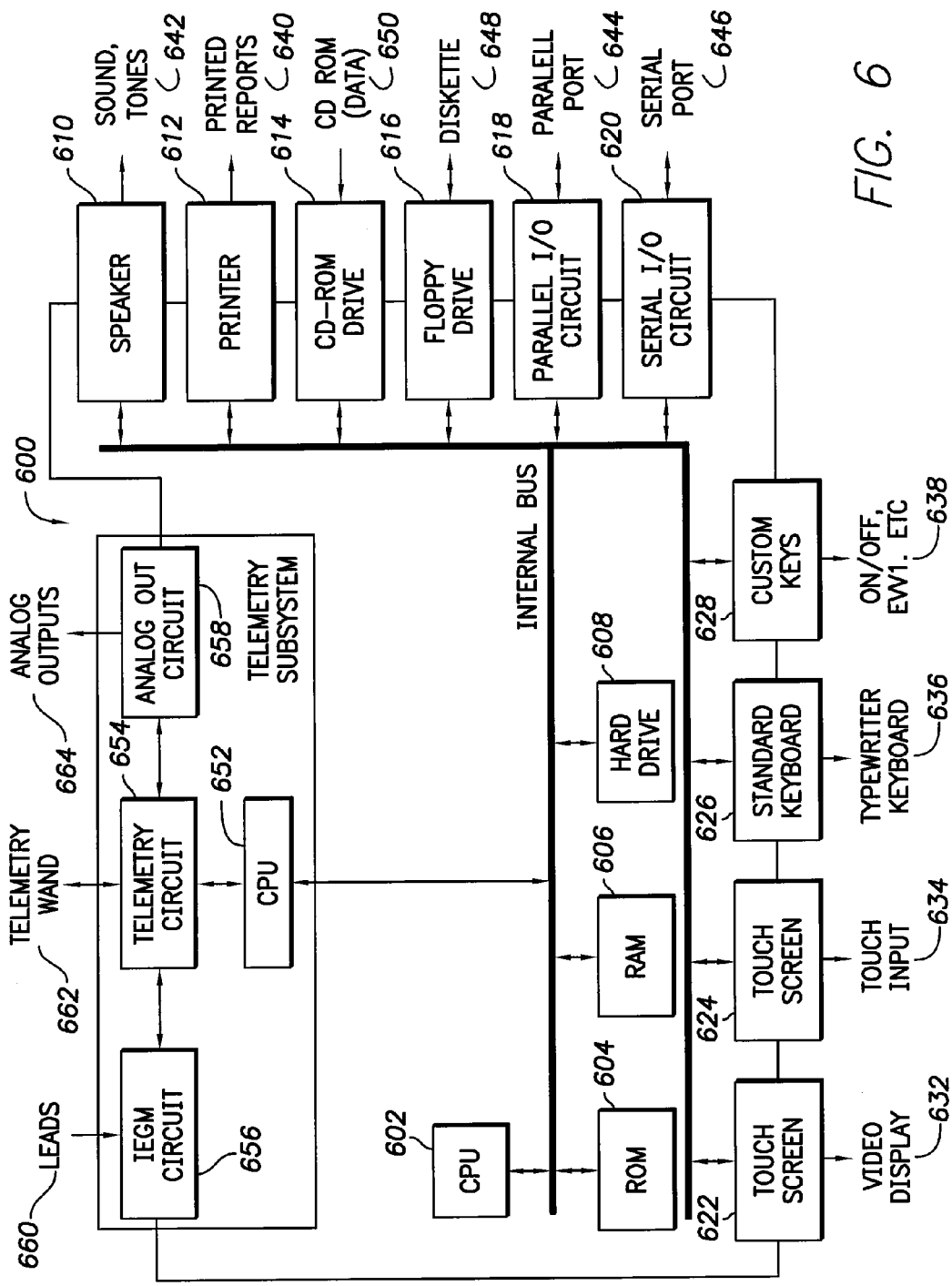
FIG. 6 illustrates a functional block diagram of the external device that is operated in accordance with the processes of FIGS. 3 and 4A-4C and to interface with IMD.

FIG. 6 illustrates a functional block diagram of the external device 600 that is operated in accordance with the processes of FIGS. 3 and 4A-4C and to interface with IMD 100. The external device 600 may be a workstation, a portable computer, an IMD programmer, a PDA, a cell phone and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates and detection thresholds.

The CPU 602 typically includes a microprocessor, a microcontroller, or equivalent control circuitry, designed specifically to control interfacing with the external device 600 and with the IMD 100. The CPU 602 performs the COI measurement process discussed above. The CPU 602 may include RAM or ROM memory, logic and timing circuitry, state machine circuitry, and I/O circuitry to interface with the IMD 100. The display 622 (e.g., may be connected to the video display 632). The touch screen 624 may display graphic information relating to the IMD 100. The display 622 displays information related to the COI measurement process, including the window 500 of FIG. 5. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 includes a central processing unit (CPU) 652 in electrical communication with a telemetry circuit 654, which communicates with both an IEGM circuit 656 and an analog out circuit 658. The circuit 656 may be connected to leads 660. The circuit 656 is also connected to the implantable leads 114, 116 and 118 to receive and process IEGM cardiac signals as discussed above. Optionally, the IEGM cardiac signals sensed by the leads 114, 116 and 118 may be collected by the IMD 100 and then transmitted, to the external device 600, wirelessly to the telemetry subsystem 630 input.

The telemetry circuit 654 is connected to a telemetry wand 662. The analog out circuit 658 includes communication circuits to communicate with analog outputs 664. The external device 600 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hardwired connection may be used to connect the external device 600 to the IMD 100.

Figure 7:
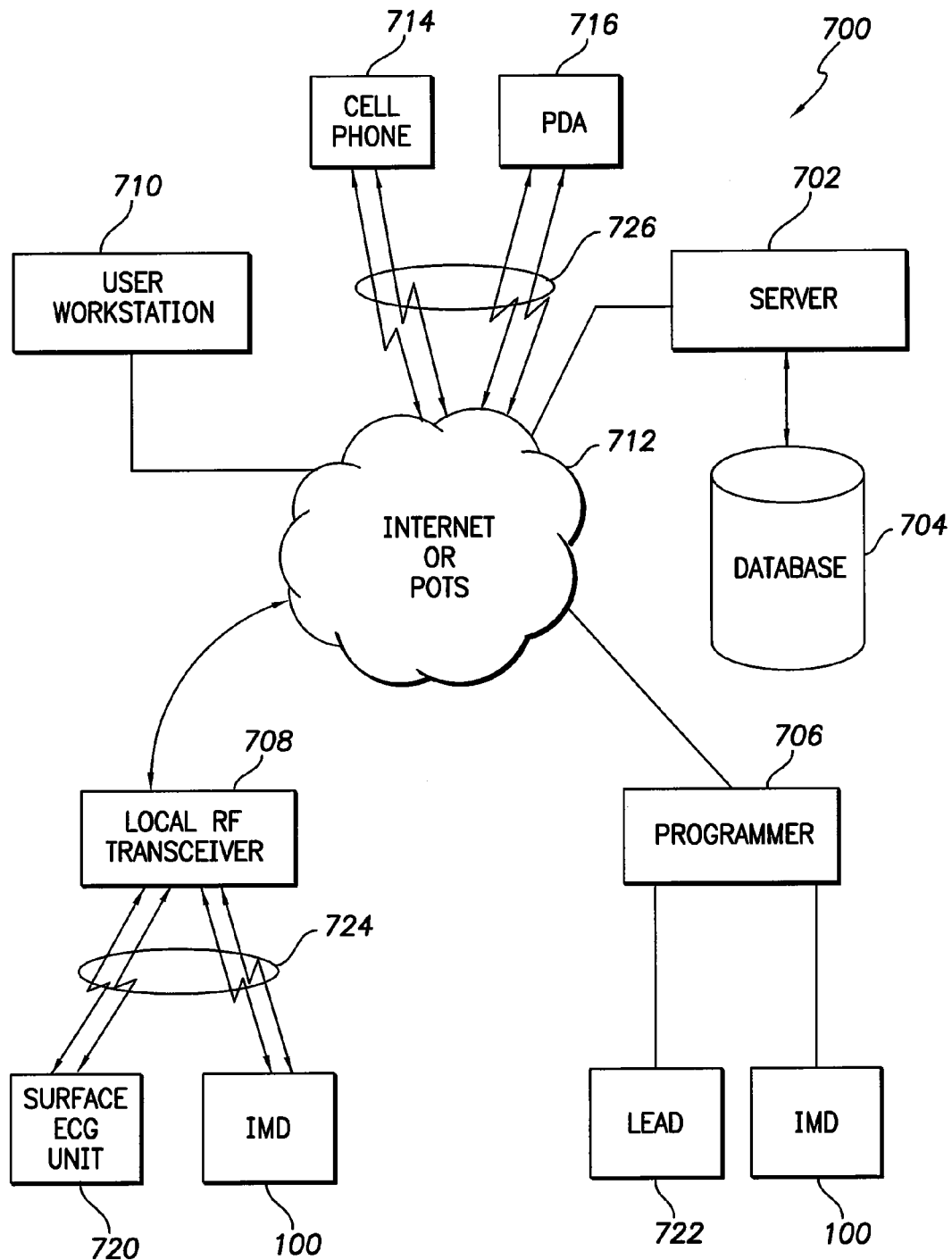
FIG. 7 illustrates a distributed processing system in accordance with one embodiment.

FIG. 7 illustrates a distributed processing system 700 in accordance with one embodiment. The distributed processing system 700 includes a server 702 connected to a database 704, a programmer 706 (e.g., similar to external device 600 (shown in FIG. 5)), a local RF transceiver 708 and a user workstation 710 electrically connected to a communication system 712. Any of the processor-based components in FIG. 7 (e.g., workstation 710, cell phone 714, PDA 716, server 702, programmer 706, IMD 100) may perform the COI measurement process discussed above.

The communication system 712 may be the internet, a voice over IP (VoIP) gateway, a local plain old telephone service (POTS) such as a public switched telephone network (PSTN), a cellular phone based network, and the like. Alternatively, the communication system 712 may be a local area network (LAN), a campus area network (CAN), a metropolitan area network (MAN), or a wide area network (WAM). The communication system 712 serves to provide a network that facilitates the transfer/receipt of information such as cardiac signal waveforms, ventricular and atrial heart rates.

The server 702 is a computer system that provides services to other computing systems over a computer network. The server 702 controls the communication of information such as cardiac signal waveforms, ventricular and atrial heart rates, and detection thresholds 246 (shown in FIG. 2). The server 702 interfaces with the communication system 712 to transfer information between the programmer 706, the local RF transceiver 708, the user workstation 710 as well as a cell phone 714 and a personal data assistant (PDA) 716 to the database 704 for storage/retrieval of records of information. On the other hand, the server 702 may upload raw cardiac signals from an implanted lead 722, surface ECG unit 722 or the IMD 100 via the local RF transceiver 708 or the programmer 706.

The database 704 stores information such as cardiac signal waveforms, ventricular and atrial heart rates, detection thresholds 246 (shown in FIG. 2), and the like, for a single or multiple patients. The information is downloaded into the database 704 via the server 702 or, alternatively, the information is uploaded to the server from the database 704. The programmer 706 is similar to the external device 600 and may reside in a patient's home, a hospital, or a physician's office. The programmer 706 interfaces with the lead 722 and the IMD 100. The programmer 706 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 706 to the IMD 100. The programmer 706 is able to acquire cardiac signals from the surface of a person (e.g., ECGs), intra-cardiac electrogram (e.g., IEGM) signals from the IMD 100, and/or cardiac signal waveforms, ventricular and atrial heart rates, and detection thresholds from the IMD 100. The programmer 706 interfaces with the communication system 712, either via the internet or via POTS, to upload the information acquired from the surface ECG unit 720, the lead 722 or the IMD 100 to the server 702.

The local RF transceiver 708 interfaces with the communication system 712 to upload one or more of cardiac signal waveforms, ventricular and atrial heart rates, and detection thresholds 246 (shown in FIG. 2) to the server 702. In one embodiment, the surface ECG unit 720 and the IMD 100 have a bi-directional connection 724 with the local RF transceiver 708 via a wireless connection. The local RF transceiver 708 is able to acquire cardiac signals from the surface of a person, intra-cardiac electrogram signals from the IMD 100, and/or cardiac signal waveforms, ventricular and atrial heart rates, and detection thresholds 246 from the IMD 100. On the other hand, the local RF transceiver 708 may download stored cardiac signal waveforms, ventricular and atrial heart rates, and detection thresholds 246, and the like, from the database 704 to the surface ECG unit 720 or the IMD 100.

The user workstation 710 may interface with the communication system 712 via the internet or POTS to download cardiac signal waveforms, ventricular and atrial heart rates, and detection thresholds 246 (shown in FIG. 2) via the server 702 from the database 704. Alternatively, the user workstation 710 may download raw data from the surface ECG units 720, lead 722 or IMD 100 via either the programmer 706 or the local RF transceiver 708. Once the user workstation 710 has downloaded the cardiac signal waveforms, ventricular and atrial heart rates, or detection thresholds, the user workstation 710 may process the information in accordance with one or more of the operations described above. The user workstation 710 may download the information and notifications to the cell phone 714, the PDA 716, the local RF transceiver 708, the programmer 706, or to the server 702 to be stored on the database 704. For example, the user workstation 710 may communicate data to the cell phone 714 or PDA 716 via a wireless communication link 726.

Figure 8:
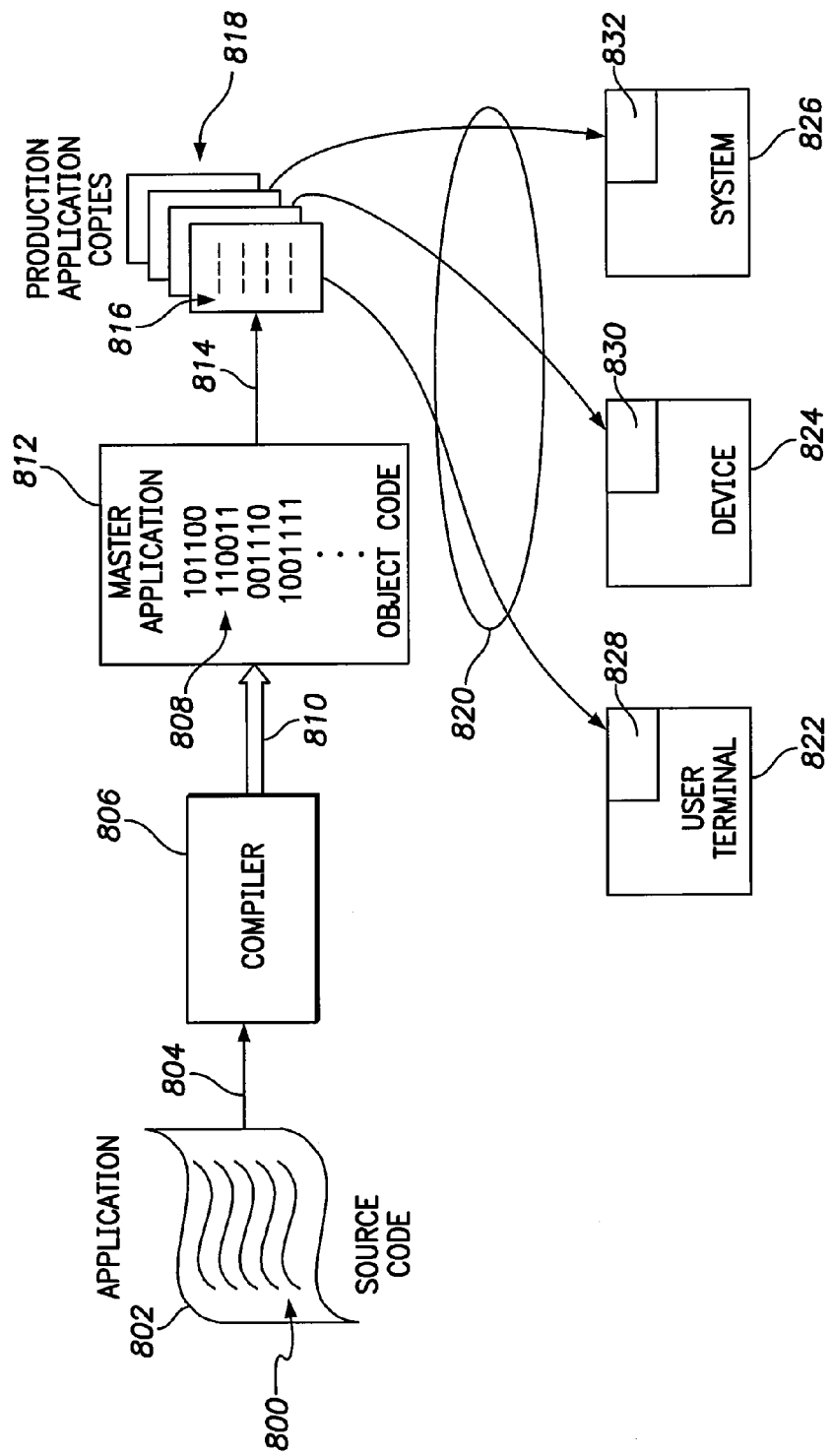
FIG. 8 illustrates a block diagram of example manners in which embodiments of the present invention may be stored, distributed, and installed on a computer-readable medium.

FIG. 8 illustrates a block diagram of example manners in which embodiments of the present invention may be stored, distributed, and installed on a computer-readable medium. In FIG. 8, the "application" represents one or more of the methods and process operations discussed above. The application is initially generated and stored as source code 800 on a source computer-readable medium 802. The source code 800 is then conveyed over path 804 and processed by a compiler 806 to produce object code 808. The object code 808 is conveyed over path 810 and saved as one or more application masters on a master computer-readable medium 812. The object code 808 is then copied numerous times, as denoted by path 814, to produce production application copies 816 that are saved on separate production computer-readable media 818. The production computer-readable media 818 are then conveyed, as denoted by path 820, to various systems, devices, terminals and the like. A user terminal 822, a device 824 and a system 826 are shown as examples of hardware components, on which the production computer-readable medium 818 are installed as applications (as denoted by 828 through 832). For example, the production computer-readable medium 818 may be installed on the IMD 100 (shown in FIG. 1) and/or the microcontroller 520 (shown in FIG. 5). Examples of the source, master, and production computer-readable medium 802, 812, and 818 include, but are not limited to, CDROM, RAM, ROM, Flash memory, RAID drives, memory on a computer system, and the like. Examples of the paths 804, 810, 814, and 820 include, but are not limited to, network paths, the internet, Bluetooth, GSM, infrared wireless LANs, HIPERLAN, 3G, satellite, and the like. The paths 804, 810, 814, and 820 may also represent public or private carrier services that transport one or more physical copies of the source, master, or production computer-readable media 802, 812 or 818 between two geographic locations. The paths 804, 810, 814 and 820 may represent threads carried out by one or more processors in parallel. For example, one computer may hold the source code 800, compiler 806 and object code 808. Multiple computers may operate in parallel to produce the production application copies 816. The paths 804, 810, 814, and 820 may be intra-state, inter-state, intra-country, inter-country, intra-continental, inter-continental, and the like.

The operations noted in FIG. 8 may be performed in a widely distributed manner world-wide with only a portion thereof being performed in the United States. For example, the application source code 800 may be written in the United States and saved on a source computer-readable medium 802 in the United States, but transported to another country (corresponding to path 804) before compiling, copying and installation. Alternatively, the application source code 800 may be written in or outside of the United States, compiled at a compiler 806 located in the United States and saved on a master computer-readable medium 812 in the United States, but the object code 808 transported to another country (corresponding to path 814) before copying and installation. Alternatively, the application source code 800 and object code 808 may be produced in or outside of the United States, but production application copies 816 produced in or conveyed to the United States (for example, as part of a staging operation) before the production application copies 816 are installed on user terminals 822, devices 824, and/or systems 826 located in or outside the United States as applications 828 through 832.

As used throughout the specification and claims, the phrases "computer-readable medium" and "instructions configured to" shall refer to any one or all of (i) the source computer-readable medium 802 and source code 800, (ii) the master computer-readable medium and object code 808, (iii) the production computer-readable medium 818 and production application copies 816 and/or (iv) the applications 828 through 832 saved in memory in the terminal 822, device 824, and system 826.

Figure 9:
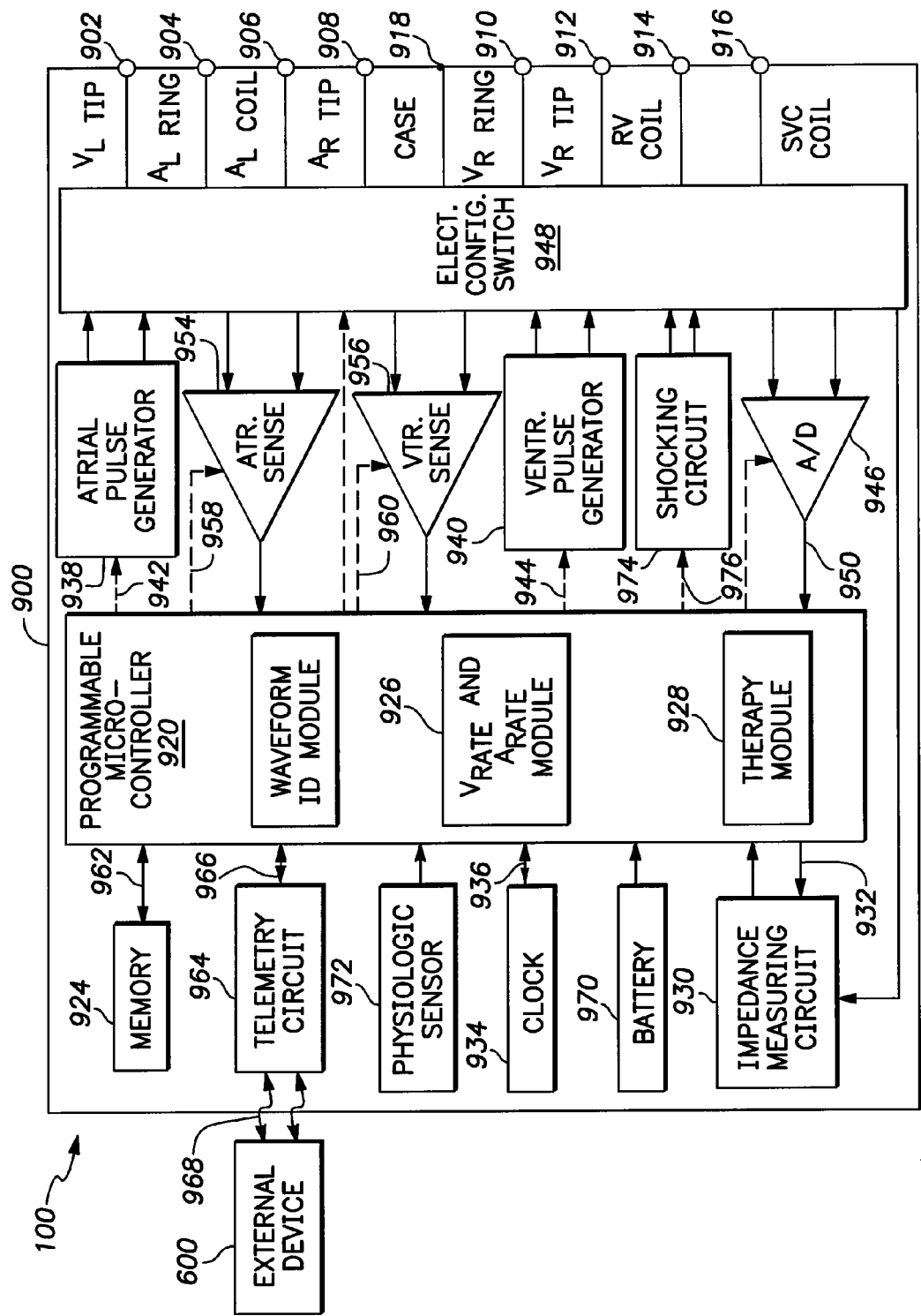
FIG. 9 illustrates a block diagram of exemplary internal components of the IMD.

FIG. 9 illustrates a block diagram of exemplary internal components of the IMD 100. The IMD 100 may collect IEGM cardiac signals from one or more leads and pass the IEGM cardiac signals to an external device 600 for COI measurement. Optionally, the IMD 100 may perform the COI measurements. The IMD 100 includes the housing 900 that includes a left ventricle tip input terminal (VL TIP) 902, a left atrial ring input terminal (AL RING) 904, a left atrial coil input terminal (AL COIL) 906, a right atrial tip input terminal (AR TIP) 908, a right ventricular ring input terminal (VR RING) 910, a right ventricular tip input terminal (VR TIP) 912, an RV coil input terminal 914 and an SVC coil input terminal 916. A case input terminal 918 may be coupled with the housing 900 of the IMD 100. The input terminals 902-918 may be electrically coupled with the electrodes 120-138 (shown in FIG. 1).

The IMD 100 includes a programmable microcontroller 920, which controls the operation of the IMD 100 based on acquired cardiac signals. The microcontroller 920 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. Among other things, the microcontroller 920 receives, processes, and manages storage of digitized data from the various electrodes (shown in FIG. 1). The microcontroller 920 may include one or more modules and processors configured to perform one or more of the operations described above in connection with the process 300.

A waveform identification module 924 examines the cardiac signal waveforms sensed by the electrodes 120-138 (shown in FIG. 1) and identifies the waveforms as being atrial or ventricular waveforms. A ventricular and atrial rate calculation module 926 calculates the ventricular heart rate VRATE and the atrial heart rate ARATE based on the cardiac signals sensed by the electrodes 120-138.

A therapy module 928 determines whether to permit or inhibit the application of one or more stimulation pulses to the heart 102 to treat tachycardia. The therapy module 928 may direct an excitation source to deliver or not deliver the stimulation pulses to the heart 102. The pulse generators 938, 940 are controlled via appropriate control signals 942, 944 to trigger or inhibit the stimulation pulses. In the case where IMD 100 is permitted by the therapy module 928 to apply stimulation pulses to the heart 102, the IMD 100 applies an appropriate electrical shock therapy to the heart. One or more of the modules 922-928 may receive signals from the electrodes 120-138 (shown in FIG. 1) via an analog-to-digital (A/D) data acquisition system 946. For example, the cardiac signals indicative of atrial and ventricular waveforms may be sensed by the electrodes 120-138 and communicated to the data acquisition system 946. The cardiac signals are communicated through the input terminals 502-516 to an electronically configured switch bank, or switch, 948 before being received by the data acquisition system 946. The data acquisition system 946 converts the raw analog data of the signals obtained by the electrodes 120-138 into digital signals 950 and communicates the signals 950 to the microcontroller 920. A control signal from the microcontroller 920 determines when the data acquisition system 946 acquires signals, stores the signals 950 in the memory 924, or transmits data to an external device 600.

The switch 948 includes a plurality of switches for connecting the desired electrodes 120-138 (shown in FIG. 1) and input terminals 502-518 to the appropriate I/O circuits. The switch 948 closes and opens switches to provide electrically conductive paths between the circuitry of the IMD 100 and the input terminals 902-918. An atrial sensing circuit 954 and a ventricular sensing circuit 956 may be selectively coupled to the leads of the IMD 100 through the switch 948 for detecting the presence of cardiac activity in the chambers of the heart. The IMD 100 additionally includes a battery 970 that provides operating power to the circuits shown within the housing 900, including the microcontroller 920. The IMD 100 includes a physiologic sensor 972 that may be used to adjust pacing stimulation rate according to the exercise state of the patient.

A clock 934 may measure time relative to the cardiac cycles or cardiac signal waveforms of the heart 102. The memory 924 may be embodied in a computer-readable storage medium such as a ROM, RAM, flash memory, or other type of memory. The microcontroller 920 is coupled to the memory 924 by a suitable data/address bus. The memory 924 may store programmable operating parameters and thresholds used by the microcontroller 920, as required, in order to customize the operation of IMD 100 to suit the needs of a particular patient. The operating parameters of the IMD 100 and thresholds may be non-invasively programmed into the memory 924 through a telemetry circuit 964 in communication with the external device 600, such as a trans-telephonic transceiver or a diagnostic system analyzer. The telemetry circuit 964 is activated by the microcontroller 920 by a control signal 966. The telemetry circuit 964 allows intra-cardiac electrograms, cardiac waveforms of interest, detection thresholds, status information relating to the operation of IMD 100, and the like, to be sent to the external device 600.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for measuring current of injury (COI) during lead fixation, the method comprising:
    sensing cardiac signals from a lead within a chamber of a heart while the lead is in a pre-fixation position;
    capturing a baseline waveform from the cardiac signals while the lead is in the pre-fixation position, the baseline waveform representative of an interface between the lead and a tissue region proximate a tip of the lead directly engaging the tissue region of the heart and before the tip of the lead is actively attached to the tissue region of the heart;
    affixing the lead to the tissue
    sensing cardiac signals from the lead within the chamber of the heart when the lead is in a post-fixation position;
    capturing a post-fixation waveform from the cardiac signals when the lead is in the post-fixation position, the post-fixation waveform representative of an interface between the lead and the tissue region proximate the tip of the lead after the lead is actively attached to the tissue region of the heart; and
    calculating a COI indicator based on an automatic comparison of the baseline and post-fixation waveforms.

2. The method of claim 1, further comprising:
    identifying a COI feature of interest in the baseline and post-fixation waveforms; and
    calculating at least one of a COI index, a COI area, a COI differential and a COI ratio based on the COI feature of interest in the baseline and post-fixation waveforms.

3. The method of claim 1, further comprising calculating a baseline COI area in the baseline waveform and a post-fixation COI area in the post-fixation waveform; and
    determining a difference between the baseline and post-fixation COI areas.

4. The method of claim 1, further comprising displaying information indicative of at least one of a COI index, a COI area, a COI differential and a COI ratio.

5. The method of claim 1, further comprising displaying the baseline and post-fixation waveforms.

6. The method of claim 1, further comprising defining an exclusion zone based on predetermined intervals before and after a peak of the R-wave in the baseline and post-fixation waveforms.

7. The method of claim 1, identifying an ST segment shift in the baseline and post-fixation waveforms following a peak of corresponding R-waves, the ST segment shift constituting a COI shift that is utilized when calculating the COI indicator.

8. The method of claim 1, further comprising:
    identifying a neutral crossing point in the baseline and post-fixation waveforms following a peak of corresponding R-waves; and
    determining a COI duration based on the neutral crossing point, the COI duration being utilized when calculating the COI indicator.

9. The method of claim 1, further comprising:
    identifying waveform features of interest (FOI); and
    aligning the baseline and post-fixation waveforms with one another based on the waveform FOI, before calculating the COI indicator.

10. The method of claim 1, further comprising scaling the baseline and post-fixation waveforms with one another.

11. The method of claim 1, further comprising aligning the baseline and post-fixation waveforms with one another based on an isoelectric level in the post-fixation waveform before calculating the COI indicator.

12. A system for measuring current of injury (COI) during lead fixation, comprising:
    inputs configured to obtain cardiac signals sensed from a lead within a chamber of a heart while the lead is in a pre-fixation position;
    memory configured to capture a baseline waveform from the cardiac signals while the lead is in the pre-fixation position, the baseline waveform representative of an interface between the lead and a tissue region proximate a tip of the lead directly engaging the tissue region of the heart and before the lead tip is actively attached to the tissue region of the heart;
    the inputs further configured to obtain cardiac signals sensed from the lead within the chamber of the heart when the lead is in a post-fixation position;
    the memory for further configured to capture a post-fixation waveform from the cardiac signals when the lead is in the post-fixation position, the post-fixation waveform representative of an interface between the lead and the tissue region proximate the tip of the lead after the lead is actively attached to the tissue region of the heart; and a processor for further configured to calculate a COI indicator based on an automatic comparison of the baseline and post-fixation waveforms.

13. The system of claim 12, the processor:
   identifying a COI feature of interest in the baseline and post-fixation waveforms; and
   calculating at least one of a COI index, a COI area, a COI differential and a COI ratio based on the COI feature of interest in the baseline and post-fixation waveforms.

14. The system of claim 12, the processor calculating a baseline COI area in the baseline waveform and a post-fixation COI area in the post-fixation waveform; and determining a difference between the baseline and post-fixation COI areas.

15. The system of claim 12, further comprising a display for displaying information indicative of at least one of a COI index, a COI area, a COI differential and a COI ratio.

16. The system of claim 12, further comprising a display for displaying the baseline and post-fixation waveforms.

17. The system of claim 12, the processor defining an exclusion zone based on predetermined intervals before and after a peak of the R-wave in the baseline and post-fixation waveforms.

18. The system of claim 12, the processor identifying an ST segment shift in the baseline and post-fixation waveforms following a peak of corresponding R-waves, the ST segment shift constituting a COI shift that is utilized when calculating the COI indicator.

19. The system of claim 12, the processor:
   identifying a neutral crossing point in the baseline and post-fixation waveforms following a peak of corresponding R-waves;
   determining a COI duration based on the neutral crossing point, the COI duration being utilized when calculating the COI indicator.

20. The system of claim 12, the processor:
   identifying waveform features of interest (FOI); and
   aligning the baseline and post-fixation waveforms with one another based on the waveform FOI, before calculating the COI indicator.

21. The system of claim 12, the processor scaling the baseline and post-fixation waveforms with one another.

22. The system of claim 12, the processor aligning the baseline and post-fixation waveforms with one another based on an isoelectric level in the post-fixation waveform before calculating the COI indicator.

* * * * *